United States Patent [19]
Archibald et al.

[11] Patent Number: 5,817,778
[45] Date of Patent: Oct. 6, 1998

[54] LARGE SCALE BATCH PROCESS FOR DIAZOMETHANE

[75] Inventors: Thomas G. Archibald, Fair Oaks; Der-Shing Huang, Folsom; Mark H. Pratton, Galt; James C. Barnard, Shingle Springs, all of Calif.

[73] Assignee: Aerojet-General Corporation, Rancho Cordova, Calif.

[21] Appl. No.: 970,035

[22] Filed: Nov. 13, 1997

[51] Int. Cl.$^6$ .................................................. C07C 245/16
[52] U.S. Cl. .......................................... 534/565; 534/558
[58] Field of Search ............................................... 534/565

[56] References Cited

U.S. PATENT DOCUMENTS 5,459,243  10/1995  Acevedo et al. ........................ 534/565

OTHER PUBLICATIONS

T.H. Black *Aldrichimica Acta,* (1983) 16(1): 3–10.
Shiga et al., Chemical Abstracts, 109:162712 (1988).
Sekiya et al., Chemical Abstracts, 92:75896 (1980).

*Primary Examiner*—Fiona T. Powers
*Attorney, Agent, or Firm*—Townsend and Townsend and Crew LLP

[57] ABSTRACT

Diazomethane is prepared in a batch process on a scale of at least 50 gram-moles per batch, from an N-methyl-N-nitroso amine in an organic solvent and an inorganic base in an aqueous solution by the use of a phase transfer catalyst and by controlling the choice of solvent, reagent concentrations, addition rate and reaction temperature to cause codistillation of the product and the organic solvent in such a manner that the concentration of diazomethane in both liquid and vapor phases are controlled within limits that will prevent detonation of the diazomethane.

19 Claims, No Drawings

LARGE SCALE BATCH PROCESS FOR DIAZOMETHANE

BACKGROUND OF THE INVENTION

1. Field of the Invention

This invention resides in the technology of diazomethane synthesis.

2. Description of the Prior Art

Diazomethane ($CH_2$=N=N, also known as azimethylene or diazirine) has a wide range of utility in chemical syntheses. It is a common methylating agent for carboxylic acids, phenols, alcohols, enols, and heteroatoms such as nitrogen and sulfur. It is also used for the ring expansion or chain extension of ketones, and for the conversion of ketones to epoxides. A further example of its use is the conversion of acid chlorides to α-diazoketones which are themselves useful intermediates. Still further examples are its use in cycloaddition reactions with olefins to produce cyclopropyl or nitrogen-containing heterocyclic rings. Still further examples involve the formation of viral protease inhibitors including those used to combat HIV. A particularly important class of viral protease inhibitors are those that include structures known as amino acid isosteres which consist of a three-carbon moiety derived from a two-carbon amino acid by the addition of a functionalized carbon. An example is Saquinavir (Roche Laboratories). The addition of the carbon must be done without compromising the chirality of the amino acid or affecting any portion of the remainder of the molecule. This is successfully achieved by the use of diazomethane in a modified Arndt-Eistert reaction.

Despite its wide applicability in chemical synthesis, diazomethane is a hazardous reagent. It is a carcinogen and a powerful allergen and is poisonous. Its greatest problem however is that it is highly explosive. For this reason, the technical literature on the synthesis of diazomethane cautions against the use of ground-glass joints and any glassware that has not been firepolished, and no syntheses other than laboratory bench-scale syntheses have been reported. Equipment specifically designed for diazomethane preparation, such as the DIAZALD® apparatus of Aldrich Chemical Company, Inc., Milwaukee, Wis., USA, is designed for a maximum of 300 millimoles of diazomethane by single batch reaction. See Black, T. H., "The Preparation and Reactions of Diazomethane," *Aldrichimica Acta* 16(1): 3–10 (1983). A preparation referred to as "large scale" is disclosed by Acevedo et al. in U.S. Pat. No. 5,459,243, "Apparatus and Processes for the Large Scale Generation and Transfer of Diazomethane," issued Oct. 17, 1995. The reactions disclosed in the patent however are performed in laboratory Erlenmeyer glassware on a 100-millimole (4.2 g) scale.

In view of the versatility of diazomethane, a truly large-scale process, i.e., one that produces quantities well into the gram-mole range in a single batch, is needed.

SUMMARY OF THE INVENTION

It has now been discovered that diazomethane can be synthesized in a batch reaction on a truly large scale with little or no danger of explosion. Batches of 50 gram-moles (2.1 kg) of diazomethane quantity or greater can now be prepared, such as about 50 gram-moles to about 25,000 gram-moles (2.1 kg to 210 kg), preferably about 100 gram-moles to about 15,000 gram-moles (4.2 kg to 126 kg), and more preferably about 300 gram-moles to about 10,000 gram-moles (12.6 kg to 42.1 kg). As in the prior art, the synthesis includes the reaction between an N-methyl-N-nitroso amine and a strong base and is conducted in a two-phase aqueous-organic liquid reaction mixture with co-distillation of the organic solvent and the product diazomethane immediately as the latter is formed. According to the invention, however, the reaction is conducted in the presence of a phase transfer catalyst, and the choice of organic solvent, the degree of dilution of the reagents in the solvent, and the reaction temperature are selected such that the concentration of diazomethane in both the liquid and vapor phases are maintained within prescribed limits of a maximum of about 3 weight percent in the liquid phase and a maximum of about 25 mole or volume percent in the vapor phase. Further insurance against spontaneous explosions is achieved by maintaining the reaction conditions steady, for example by adding an organic solution of the N-methyl-N-nitroso amine at a gradual and steady rate to the aqueous base, and by maintaining controlled agitation of the reaction mixture during the addition to avoid localized variations in concentration and temperature within the reaction vessel.

Further features, embodiments and advantages of the invention will become apparent from the description that follows.

DETAILED DESCRIPTION OF THE INVENTION AND PREFERRED EMBODIMENTS

The phase transfer catalyst is any catalyst that will dissolve in the two-phase liquid system and enhance the rate of reaction between a reactant in the aqueous phase and one in the organic phase. Any of the wide variety of known phase transfer catalysts will serve this purpose, although the preferred catalysts are those that will neither undergo a chemical decomposition nor vaporize into the gas phase under the conditions at which the reaction is performed. High-boiling phase transfer catalysts, preferably with boiling points above about 200° C., are preferred.

Examples of classes of phase transfer catalysts that can be used are quaternary ammonium or phosphonium salts, crown ethers and glycol ethers. Examples of quaternary ammonium salts are benzyltriethylammonium chloride, methyltrioctylammonium chloride, methyltrioctylammonium bromide, tetra-n-butylammonium chloride, tetra-n-butyl-ammonium bromide, and other such ammonium halides containing 15 or more carbon atoms. Examples of quaternary phosphonium salts are tetra-n-butylphosphonium chloride, tetra-n-butylphosphonium bromide, and others that are the phosphonium counterparts to the quaternary ammonium salts. Note however that in preferred embodiments of this invention, the reaction is performed at a temperature in excess of 45° C. and in very strong base. Under these conditions, quaternary amonium salts are often degraded to amines which would react with diazomethane. Hence, quaternary ammonium salts that degrade in this manner are less preferred than other phase transfer catalysts.

Examples of crown ethers are hexaoxacyclooctodecane and its analogs with phenyl and cyclohexyl ring substituents on the crown ether ring. Examples of glycols are diethylene glycol monomethyl ether, diethylene glycol monoethyl ether, triethylene glycol monomethyl ether, and triethylene glycol monoethyl ether. Glycols having a molecular weight of at least about 120 are preferred. One particularly effective glycol for this purpose is diethylene glycol monoethyl ether.

The phase transfer catalyst is employed in a catalytic amount, which is generally a range of concentrations. The optimum amount or preferred range in any particular system will vary with the particular catalyst or class of catalyst used, but the appropriate amount for any particular reaction system will be apparent to those skilled in the use of these catalysts.

The N-methyl-N-nitroso amine used in the process of this invention is represented generically by the formula

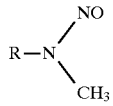

in which R is an electron-withdrawing radical, or a radical with an electron-withdrawing group in close proximity (preferably bonded directly) to the amine nitrogen at the center of the formula. Examples of electron-withdrawing groups are sulfonyl groups (—SO$_2$—), carbonyl groups (—C(=O)—), and iminomethylene groups (—C(=NH)—). Examples of specific N-methyl-N-nitroso amines within the above formula are N-methyl-N'-nitro-N-nitrosoguanidine (commonly known as "MNNG"), N-methyl-N-nitrosourea, N-methyl-N-nitrosocarbamate, N-methyl-N-nitrosourethane, and N-methyl-N-nitroso-p-toluene-sulfonamide (available from Aldrich Chemical Company, Inc., Milwaukee, Wis., USA, as "DIAZALD®").

The choice of inorganic base is not critical to the invention, although the preferred inorganic base is potassium hydroxide.

The organic solvent is selected as one that will co-distill with the diazomethane in a manner that will reduce or eliminate the risk of a high concentration of diazomethane in the vapor phase. Examples of solvents that are useful for this purposes are ethers, diethers, alkanes, and hydrocarbon mixtures such as petroleum ethers with boiling temperatures below about 50° C. Ethers are preferred, and the most effective ethers and solvents in general are those with boiling points less than about 40° C. Examples are diethyl ether, methyl ethyl ether, and methyl propyl ether. The most preferred is diethyl ether.

The process of this invention is conducted by adding the N-methyl-N-nitroso amine as a solution in the organic solvent to a temperature-controlled aqueous solution of the inorganic base and phase transfer catalyst. The concentration of the N-methyl-N-nitroso amine in the organic solvent, the concentration of the inorganic base in the aqueous solution, the rate of addition of the organic phase to the aqueous phase, and the temperature at which the reaction mixture is maintained through the course of the addition are all maintained at levels that will limit the diazomethane concentrations in the liquid and vapor phases to non-explosive levels. These levels will be selected in accordance with known relations, which will vary with the choice of organic solvent but are otherwise within the expertise of those knowledgeable of the properties of these substances and skilled in the art of using them. The temperature in the reaction vessel, for example, is preferably maintained within the range of about 45° C. to about 55° C., and most preferably within the range of about 48° C. to about 52° C., particularly with diethyl ether as the solvent. To maintain these conditions, the reaction vessel can be equipped with an electronic interlock designed to prevent the addition of the N-methyl-N-nitrosoamine when the temperature of the reaction mixture falls below 45° C. This will prevent a vapor phase from forming that is too low in vaporized solvent content and hence too high in diazomethane content. With N-methyl-N-nitroso-p-toluenesulfonamide as the N-methyl-N-nitroso amine and diethyl ether as the solvent, for example, the concentration of the N-methyl-N-nitroso-p-toluenesulfonamide in the ether is preferably maintained within the range of from about 18% to about 25% by weight. The concentration of the inorganic base is preferably within the range of about 40% to about 50% by weight.

In the preferred practice of this invention, therefore, the concentrations of the starting solutions, the operating temperature, and the rate of addition of the organic phase to the reaction vessel are selected such that the concentration of diazomethane in the vapor phase is maintained below about 25% on a mole basis, preferably from about 1% to about 24%, and most preferably from about 15% to about 23%. With diethyl ether as the organic solvent, the diazomethane concentration in the liquid phase should remain at less than about 3% by weight, preferably from about 1% to about 3%.

Uniformity in temperature and composition of the reaction mixture is preferably maintained by gentle agitation. Conventional agitators, preferably mechanical rotators, can be used. In general, conventional chemical process equipment can be used throughout this process.

The vapor phase evolved from the reaction is cooled by a condenser that is maintained at a temperature low enough to maintain a low diazomethane concentration in both the vapor phase and the condensate. Both the condenser and the receiving vessel for the condensate should be maintained at a temperature below the boiling point of diazomethane (−23° C.). Preferably, the condenser and receiving vessel are maintained at −30° C. or below.

Despite the ability to perform a safe, non-explosive reaction under the conditions and procedures described above, additional precautions can be taken to assure that no explosions occur. It is important, for example, to purge the equipment with the organic solvent both before and after the start of diazomethane generation to assure that the diazomethane is always formed in the presence of organic vapor of high heat capacity. As explained above, the solvent must be one that vaporizes and condenses at a temperature that maintains the vapor phase diazomethane concentration within safe limits. The most dangerous site in the apparatus is the point at which the diazomethane recondenses at the entry to the reaction vessel, since the vapor phase diazomethane concentration is high at this point. The continuous and rapid flow of the mixture of solvent and diazomethane vapors into the condenser pushes the diazomethane through the condenser and into the cool (approximately −20° C. to −30° C.) reactor. If the distillation were discontinued, the condition of the reactor would be dangerous but could be rendered safe again by cooling the solvent/diazomethane mixture to −20° C.

In addition, residual diazomethane can be removed and rendered innocuous by reaction with acid to liberate nitrogen and methyl compounds. Preferred acids are organic acids, of which the most preferable is acetic acid. Aqueous acetic acid at a concentration of approximately 20% is typical for this purpose. The products of the reaction of diazomethane with acetic acid are nitrogen gas and methyl acetate. Thus, at the end of a batch reaction, all residual or excess diazomethane is preferably removed by flushing the reactor and all feed and exit lines with concentrated aqueous acetic acid and purging the equipment with nitrogen gas for thirty minutes or more. It is also advisable to allow the air surrounding the reactor to be replaced by fresh air before starting a second batch.

As a further precaution, the reactor and overhead lines should be designed such that empty space in the reactor and overhead lines is limited to minimize the total quantity of diazomethane present. In addition, the reactor and the connecting flow conduits should be designed to eliminate dead spaces and wall sections where the temperature differs from surrounding areas. This will help avoid the accumulation of diazomethane and localized fractional distillation which could cause localized high concentrations.

Ground glass joints need not be avoided in the practice of this invention. Common laboratory flasks with ground glass joints can indeed be used. In larger scale production, conventional reactor vessels can be used, such as glass-lined steel vessels supplied by Pfaudler—U.S., Inc., Alloy Products, Rochester, N.Y., USA. On repetitive use, however, an accumulation of polyethylene from the decomposition of diazomethane may be deposited at ground glass joints and other sites of similar character. Deposited polyethylene has the potential of impairing the sealing of joints and of providing space for vapors and liquids to accumulate. The polyethylene can be removed by heat treatment or mechanical abrasion. In addition, the apparatus should be cleaned thoroughly with acid and purged with nitrogen as described above.

It is prudent to provide the apparatus itself with the means to decompose any residual diazomethane at any time and to decontaminate all equipment exposed to diazomethane. This is accomplished by providing the means for adding acids to any diazomethane-generating vessel and any portion of the apparatus where diazomethane is present at any time during the process. As indicated above, the preferred acid is acetic acid. To accomplish this, the reactor and condensate vessel can both be equipped with input lines for acid, or for both acid and nitrogen, with conventional means for pumping or releasing the acid or the acid and nitrogen into the vessels in the event of an equipment failure. An acid scrubber can also be used to similar purpose.

Diazomethane prepared by the process of this invention can be used directly in a subsequent synthesis procedure as soon as the diazomethane is formed. This is readily achieved by condensing the diazomethane and accompanying solvent directly into a reaction vessel where subsequent reaction (in which the diazomethane itself reacts with further reactant(s)) takes place. If the diazomethane is not to be used directly, it can be dried and transferred to a cooled storage vessel. Diazomethane prepared by the process of this invention generally contains less than 1% water by weight. In the event that anhydrous diazomethane is required, the condensate can be collected over solid pellets of sodium hydroxide, potassium hydroxide, or other suitable drying agent, which are known to those skilled in the art of diazomethane synthesis, in an ice bath (less than $-30°$ C.). The pellets are preferably covered with solvent (preferably diethyl ether) to avoid an exothermic effect upon initial contact. When it is needed for use in a subsequent reaction, the dried diazomethane can then be transferred to a suitable reaction vessel by remote decantation, vacuum transfer or pump.

Regardless of the relative safety of the process of this invention, one should always remember that diazomethane is an explosive and toxic substance. Those performing the process of this invention in any of its various embodiments should undergo a comprehensive hazards evaluation and process safety management review prior to performing the process. Medical supervision and appropriate personal protective equipment are needed, and all equipment must be decontaminated prior to use.

The following examples are offered only for purposes of illustration.

EXAMPLES

A series of batch reactions were performed in reactors of various different sizes. The following process description applies to a reaction vessel of 5-liter capacity.

A clean 5-liter three-neck flask fitted with a distillation head, thermocouple, two entry ports and mechanical stirring is heated on a hot water bath. The distillation head is connected to a $-30°$ C. condenser. The exit of the condenser is connected to a 12-liter receiver vessel cooled to $-30°$ C. Attached to the receiver vessel is a second condenser that is also cooled to $-30°$ C and that is attached to an acetic acid scrubber. The receiver vessel is fitted with a thermocouple, an emergency entry port for acid quench, and mechanical stirring. All equipment is located behind explosion-proof barriers, and reagents are pumped in remotely using TEFLON transfer lines.

The diazomethane generator (the 5-liter three-neck flask) is charged with 1.7 liters of diethylene glycol monoethyl ether (DGME), 200 mL of diethyl ether, and 765 g of 40% aqueous potassium hydroxide (5.46 mole). The contents of the flask are heated to $45°$ C. and all personnel are removed from the reactor area. A solution of 990 g (4.62 mole) of N-methyl-N-nitroso-p-toluenesulfonamide (DIAZALD) in 5.8 liters of diethyl ether is added remotely at a rate such that the internal temperature of the flask is kept at $45°$ C. or above. When the addition is complete, the apparatus is rinsed with 100 mL of fresh diethyl ether. The temperature of the reaction flask is increased until the ether distillate is colorless.

When the distillate is colorless, heat to the reaction vessel is decreased and the apparatus is quenched with acetic acid until the color is gone and the quenched mixture is acidic. The yield of diazomethane varied from 70% to 85%, based on starting DIAZALD.

A series of runs following these procedures but at larger scale were performed, and the amounts used and product yield are listed in the following table.

| Reaction Vessel Size | Number of Runs | Starting Materials | | | | Diazomethane Produced (Averaged Over Number of Runs) | |
|---|---|---|---|---|---|---|---|
| | | Ether (kg) | DIA-ZALD (kg) | KOH (kg) | DGME (kg) | (kg) | (moles) |
| 12-liter | 15 | 11 | 2.7 | 0.8 | 4.5 | 0.37 | 8.8 |
| 22-liter | 450 | 15 | 3.5 | 1 | 6 | 0.48 | 11.4 |
| 200-gallon | 110 | 160 | 30 | 12 | 67 | 5.33 | 127 |
| 300-gallon | 50 | 300 | 92 | 19 | 150 | 9.78 | 233 |

No denotations occurred in any of these runs.

The following description illustrates a plant-scale implementation of the process of this invention. The description further incorporates a reaction vessel in which the product diazomethane is used directly as a reactant in a subsequent reaction.

The reaction materials (a liquid solution) that will be reacted with the product diazomethane are placed in a 750-gallon glass-lined reactor. The solution is cooled to $-30°$ C. and maintained in this condition ready to receive the diazomethane.

A 500-gallon glass-lined reaction vessel is charged with 180 kg (0.84 kg-mole) of DIAZALD dissolved in 739.2 kg (9.97 kg-moles) of diethyl ether. The temperature of this mixture is maintained above $20°$ C. to prevent precipitation of the DIAZALD. Separately, a 300-gallon stainless steel reactor is charged with 114 kg (1.015 kg-moles) of KOH, 316.42 kg (2.361 kg-moles) of DGME, 34.47 kg (0.465 kg-mole) of diethyl ether, and 20.02 kg (1.112 kg-moles) of water. The DIAZALD-diethyl ether mixture is fed to the KOH mixture at a controlled rate while maintaining the KOH mixture at a temperature of 48°–52° C.

The product diazomethane is co-distilled with the diethyl ether from the stainless steel reactor, and enters a glass condenser, where the diazomethane and the diethyl ether are both condensed. The condensate is fed to the 750-gallon glass-lined reactor containing the reaction materials for reaction with diazomethane, maintained at −30° C. and supplied with continuous agitation. The reaction between these materials and the diazomethane occurs rapidly, and agitation is continued for thirty minutes. Acetic acid is then added to both reactors to destroy any remaining diazomethane.

The foregoing is offered primarily for purposes of illustration. It will be readily apparent to those skilled in the art that the operating conditions, materials, proportions and procedural steps and other parameters of the process described herein may be further modified or substituted in various ways without departing from the spirit and scope of the invention.

We claim:

1. A process for the production of diazomethane, comprising:
   (a) adding a solution of at least about 50 g-moles of an N-methyl-N-nitroso amine of the formula

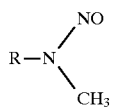

in which R is an electron-withdrawing radical, in an organic solvent that (ii) forms a separate phase when contacted with water and (i) has a boiling point less than about 40° C., to a reaction vessel containing an aqueous solution of an excess of inorganic base relative to said N-methyl-N-nitroso amine and a phase transfer catalyst, while maintaining the contents of said reaction vessel at a temperature high enough to vaporize both said organic solvent and diazomethane thus formed, the rate of addition of said N-methyl-N-nitroso amine and the temperature of said reaction vessel maintained such that the diazomethane concentration in the liquid phase in said reaction vessel is maintained at 3 weight percent or less and the diazomethane concentration in the vapor phase thus formed is maintained at about 25 mole percent or less; and
   (b) condensing said vapor phase thus formed in (a) to form an organic liquid solution of diazomethane.

2. A process in accordance with claim 1 in which said diazomethane concentration in the vapor phase is maintained at from about 1 mole percent to about 24 mole percent.

3. A process in accordance with claim 1 in which said diazomethane concentration in the vapor phase is maintained at from about 15 mole percent to about 23 mole percent.

4. A process in accordance with claim 1 in which R is a radical the portion of which that is bonded to the amine nitrogen atom shown in said formula is a member selected from the group consisting of —SO$_2$—, —C(=O)—, and —C(=NH)—.

5. A process in accordance with claim 1 in which said N-methyl-N-nitroso amine is a member selected from the group consisting of N-methyl-N'-nitro-N-nitrosoguanidine, N-methyl-N-nitrosourea, N-methyl-N-nitrosocarbamate, N-methyl-N-nitrosourethane, and N-methyl-N-nitroso-p-toluenesulfonamide.

6. A process in accordance with claim 1 in which said N-methyl-N-nitroso amine is N-methyl-N-nitroso-p-toluenesulfonamide.

7. A process in accordance with claim 1 in which said inorganic base is potassium hydroxide.

8. A process in accordance with claim 1 in which said phase transfer catalyst is a member selected from the group consisting of quaternary ammonium salts, quaternary phosphonium salts, crown ethers and glycol ethers, that will not decompose or vaporize at the temperature at which said reaction vessel of (a) is maintained.

9. A process in accordance with claim 1 in which said phase transfer catalyst is a glycol ether having a molecular weight of at least about 120.

10. A process in accordance with claim 1 in which said phase transfer catalyst is a member selected from the group consisting of diethylene glycol monomethyl ether, diethylene glycol monoethyl ether, triethylene glycol monomethyl ether, and triethylene glycol monoethyl ether.

11. A process in accordance with claim 1 in which said phase transfer catalyst is diethylene glycol monoethyl ether.

12. A process in accordance with claim 1 in which said organic solvent is an ether.

13. A process in accordance with claim 1 in which said organic solvent is a member selected from the group consisting of diethyl ether, methyl ethyl ether, and methyl propyl ether.

14. A process in accordance with claim 1 in which said organic solvent is diethyl ether.

15. A process in accordance with claim 1 in which said organic solvent is diethyl ether and said temperature maintained in said reaction vessel of (a) is from about 45° C. to about 55° C.

16. A process in accordance with claim 1 in which said organic solvent is diethyl ether and said temperature maintained in said reaction vessel of (a) is from about 48° C. to about 52° C.

17. A process in accordance with claim 1 in which said organic solvent is diethyl ether, said N-methyl-N-nitroso amine is N-methyl-N-nitroso-p-toluenesulfonamide, and the concentration of said N-methyl-N-nitroso-p-toluenesulfonamide in said diethyl ether is from about 18% to about 25% by weight.

18. A process in accordance with claim 1 in which said inorganic base is potassium hydroxide, and the concentration of said potassium hydroxide in said aqueous solution is from about 40% to about 50% by weight.

19. A process in accordance with claim 1 in which said organic solvent is diethyl ether, said N-methyl-N-nitroso amine is N-methyl-N-nitroso-p-toluenesulfonamide, said inorganic base is potassium hydroxide, said phase transfer catalyst is diethylene glycol monoethyl ether, the concentration of said N-methyl-N-nitroso-p-toluenesulfonamide in said diethyl ether is from about 18% to about 25% by weight, the concentration of said potassium hydroxide in said aqueous solution is from about 40% to about 50% by weight, and the temperature maintained in said reaction vessel of (a) is from about 48° C. to about 52° C.

* * * * *